(12) United States Patent
Chen et al.

(10) Patent No.: US 11,187,683 B2
(45) Date of Patent: Nov. 30, 2021

(54) DEXRAZOXANE ANALYTICAL METHOD

(71) Applicant: JIANGSU AOSAIKANG PHARMACEUTICAL CO., LTD., Jiangsu (CN)

(72) Inventors: Xiangfeng Chen, Nanjing (CN); Hongyu Chen, Nanjing (CN); Shuaihua Tian, Nanjing (CN); Min Sun, Nanjing (CN); Changjun Fan, Nanjing (CN)

(73) Assignee: JIANGSU AOSAIKANG PHARMACEUTICAL CO., LTD., Nanjing (CN)

( * ) Notice: Subject to any disclaimer, the term of this patent is extended or adjusted under 35 U.S.C. 154(b) by 200 days.

(21) Appl. No.: 16/465,441

(22) PCT Filed: Nov. 30, 2017

(86) PCT No.: PCT/CN2017/113985
§ 371 (c)(1),
(2) Date: May 30, 2019

(87) PCT Pub. No.: WO2018/107975
PCT Pub. Date: Jun. 21, 2018

(65) Prior Publication Data
US 2020/0003737 A1  Jan. 2, 2020

(30) Foreign Application Priority Data

Dec. 13, 2016 (CN) .......................... 201611144392.4

(51) Int. Cl.
*G01N 30/06* (2006.01)
*C07D 403/06* (2006.01)
*G01N 30/02* (2006.01)

(52) U.S. Cl.
CPC ........... *G01N 30/06* (2013.01); *C07D 403/06* (2013.01); *G01N 2030/027* (2013.01)

(58) Field of Classification Search
None
See application file for complete search history.

(56) References Cited

U.S. PATENT DOCUMENTS 3,817,980 A  6/1974  Vorbruggen et al.
2002/0117447 A1*  8/2002  Wheat .................. B01D 15/166
                                                     210/656

(Continued)

FOREIGN PATENT DOCUMENTS

CN  101948493 A  1/2011
CN  101987858 A  3/2011

(Continued)

OTHER PUBLICATIONS

Schroeder, Patricia E. et al., "Metabolism of Dexrazoxane (ICRF-187) Used as a Rescue Agent in Cancer Patients Treated With High-Dose Etoposide", Cancer Chemother Pharmacol, (2003), vol. 52, pp. 167-174.

(Continued)

*Primary Examiner* — Paul M. West
*Assistant Examiner* — Mark A Shabman
(74) *Attorney, Agent, or Firm* — Oliff PLC

(57) ABSTRACT

A high performance liquid chromatography method used for dexrazoxane-related substances is provided, and in the method, a low-density bonding reversed-phase C18 chromatographic column resistant to pure water is employed; a gradient elution is carried out with mobile phase A and mobile phase B as eluents, the mobile phase A being a buffer, and the mobile phase B being an organic solvent; the volume percent of mobile phase A in eluents in a first stage of the gradient elution is not lower than 90%, and the duration of (Continued)

the first stage of the gradient elution ranges from 15~30 minutes. By means of the analytical method, dexrazoxane is effectively separated from main impurities, and the qualities of the active pharmaceutical ingredients of dexrazoxane and the preparations thereof could be better controlled.

15 Claims, 6 Drawing Sheets

(56) References Cited

U.S. PATENT DOCUMENTS

2008/0118932 A1* 5/2008 Toler ............... A61L 24/0042
　　　　　　　　　　　　　　　　435/7.1
2010/0230355 A1* 9/2010 Kerr ................. G01N 30/38
　　　　　　　　　　　　　　　　210/657

FOREIGN PATENT DOCUMENTS

| CN | 102216315 A | 10/2011 |
|---|---|---|
| CN | 103393609 A | 11/2013 |
| CN | 103524584 A | 1/2014 |
| CN | 104177301 A | 12/2014 |
| WO | 2007/062076 A2 | 5/2007 |

OTHER PUBLICATIONS

Hasinoff, Brian B., "An HPLC and Spectrophotometric Study of the Hydrolysis of ICRF-187 (Dexrazoxane, (+)-1,2-Bis(3,5-Dioxopiperazinyl-L-YL)Propane) and Its One-Ring Opened Intermediates", International Journal of Pharmaceutics, (1994), vol. 107, pp. 67-76.

Feb. 24, 2018 Search Report issued in International Patent Application No. PCT/CN2017/113985.

* cited by examiner

DEXRAZOXANE ANALYTICAL METHOD

TECHNICAL FIELD

The present invention relates to the field of pharmaceutical analysis technique, specifically, the present invention relates to a high-performance liquid chromatography method used for dexrazoxane-related substances.

BACKGROUND

The chemical name of dexrazoxane is (S)-(+)-4,4'-(1-methyl-1,2-ethanediyl)-bis-2,6-piperazinedione, the structural formula of which is:

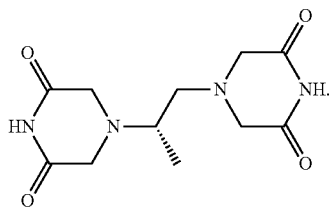 [SMILES: C[C@@H](CN1CC(=O)NC(=O)C1)N1CC(=O)NC(=O)C1]

Dexrazoxane is the dextroisomer of razoxane, also known as Dexrazoxane, Dexrazoxane or ICRF-187, which is the lipophilic derivative of a chelating agent, ethylenediamine tetraacetic acid, clinically used as a chemical protectant, and primarily used for preventing the cardiotoxicity induced by anthracyclines. The mechanism of causing the cardiotoxicity by anthracyclines is mainly due to the active oxygen is generated during the formation of a stable complex between anthracyclines and irons, which causes the lipid peroxidation to the myocardium, thus damaging the myocardium. Dexrazoxane, as the cardiac protectants against the chemotherapeutics, reduces the generation of oxygen free radicals causing the toxic effects on the myocardial tissues and thus lowers the cardiotoxicity of anthracyclines, through capturing free irons and irons in the iron-anthracyclines complexes. Dexrazoxane was developed by Chiron Co., USA, marketed first in Italy in 1992, and marketed in USA in 1995 approved by FDA. Currently, dexrazoxane is the only protectant useful for decreasing the cardiotoxicity induced by anthracycline anti-tumor drugs.

Patent WO2007/062076 disclosed that there are three main degradation impurities from dexrazoxane; Patent literature CN201310326280.0 disclosed a method for determining the impurities and contents of dexrazoxane lyophilized compositions, which employed octadecyl silane bonded silica gel as the packing, with methanol-a solution of potassium dihydrogen phosphate at 0.01 mol/L (15:85) as the mobile phase.

The existing chromatography technology is poor in the capability of separating impurities from the active pharmaceutical ingredients or preparations of dexrazoxane, with the resolution being not compliant; the retention times of the impurities are too short to achieve the purpose of separation; the amounts of impurities detected are very few, currently only 3-4 impurities could be detected by the prior art, with great difference from the actual amounts of impurities. There is a great demand in the field for a new analytical method for dexrazoxane, allowing it to analyze the active pharmaceutical ingredients of dexrazoxane or the related substances in its preparations efficiently, briefly and rapidly, thus better controlling the qualities of the products.

SUMMARY OF THE INVENTION

To solve the problems of the prior art, the present invention provides a new analytical method for dexrazoxane, which employs the gradient elution to achieve efficient separation between impurities as well as between impurities and main peaks, and is useful for the analysis on the active pharmaceutical ingredients of dexrazoxane and related substances in its preparations (such as lyophilized powder injections and other dosage forms).

The present invention primarily employs the following technical solutions:

A high-performance liquid chromatography method used for dexrazoxane-related substances, in which a low-density bonding reversed-phase C18 chromatographic column resist to pure water is employed; a gradient elution is carried out with a mobile phase A and a mobile phase B as the eluents, the mobile phase A being a buffer, and the mobile phase B being an organic solvent; the volume percent content of the mobile phase A in a first stage of the gradient elution is not lower than 90%, and the duration in the first stage of the gradient elution ranges from 15~30 minutes.

Preferably, the low-density bonding reversed-phase C18 chromatographic column resist to pure water employed in the present invention is Waters Atlantis T3 or Waters ACQUITY HSS T3; more preferably, the low-density bonding reversed-phase C18 chromatographic column resist to pure water is Waters Atlantis T3; further preferably, the specifications of the Waters Atlantis T3 is (250 mm×4.6 mm), 5 μm column.

The analytical method of the present invention performs the elution in a manner of gradient, with a mobile phase A and a mobile phase B as the eluents, the mobile phase A being a buffer, the mobile phase B being an organic solvent.

Preferably, the buffer is selected from the buffered salt solution of potassium dihydrogen phosphate, sodium dihydrogen phosphate, disodium hydrogen phosphate, dipotassium hydrogen phosphate, diammonium hydrogen phosphate or ammonium dihydrogen phosphate; more preferably, the buffer is a solution of potassium dihydrogen phosphate or sodium dihydrogen phosphate; further preferably, the buffer is a solution of potassium dihydrogen phosphate. Preferably, the buffer can be present at a concentration of 1~50 mmol/L, at a pH of 1~6; more preferably, at a concentration of 5~15 mmol/L, at a pH of 3.5~5.5; and further preferably at a concentration of about 8~12 mmol/L, at a pH of about 4.5~5. In a specific embodiment of the present invention, the buffer is a solution of potassium dihydrogen phosphate of 10 mmol/L at a pH of 4.5~5.

Preferably, the organic solvent is selected from methanol, acetonitrile or isopropanol; more preferably, the organic solvent is methanol or acetonitrile; further preferably the organic solvent is methanol.

Preferably, the volume percent content of the mobile phase A in the first stage of gradient elution is not lower than 95%, the duration of the first stage ranges from 15~20 minutes. More preferably, the volume percent content of the mobile phase A in the first stage is not lower than 98%, the duration ranges from 15 to 18 minutes. In the first stage of the gradient elution, three main degradation impurities of dexrazoxane are successively eluted to peak out. "The first stage" in the present invention refers to a period of time after the gradient elution starts, for example from time point 0 minute to 15 minutes, from time point 0 minute to 20 minutes, from time point 0 minute to 30 minute, or the like. The duration of the first stage generally ranges from 15~30 minutes, preferably ranges from 15~20 minutes. In a specific embodiment of the present invention, the duration of the first stage is 15 minutes.

Preferably, the conditions of the gradient elution are specifically:

|  | Time (minutes) | Mobile Phase A (%) | Mobile Phase B (%) |
|---|---|---|---|
| The First Stage | 0 | 100 | 0 |
|  | 15 | 100 | 0 |
|  | 45 | n | 100-n |
|  | 50 | n | 100-n |
|  | 50.01 | 100 | 0 |
|  | 60 | 100 | 0 | wherein 10≤n≤90; preferably, 60≤n≤80; further preferably, 60≤n≤80. In a specific embodiment of the present invention, n=70. the conditions of the gradient elution are as follows:

|  | Time (minutes) | Mobile Phase A (%) | Mobile Phase B (%) |
|---|---|---|---|
| The First Stage | 0 | 100 | 0 |
|  | 15 | 100 | 0 |
|  | 45 | 70 | 30 |
|  | 50 | 70 | 30 |
|  | 50.01 | 100 | 0 |
|  | 60 | 100 | 0 |

Preferably, in the analytical method of the present invention, there are also the following optional chromatographic conditions:

The flow rate of the mobile phase is 0.6~1.5 mL/min, more preferably is 0.8~1.2 mL/min, and/or The temperature of the chromatographic column is 5~20° C., preferably is 10~20° C., and/or An ultraviolet detector is employed as the detector, with a detection wavelength of 200~220 nm, preferably of 203~213 nm.

In a specific embodiment of the present invention, the flow rate of the mobile phase is 1.0 mL/min; the temperature of the chromatographic column is 15° C.; the detection wavelength is 208 nm.

It should be known to those skilled in the art that, in addition to the above ultraviolet detector, other common types of high-performance liquid chromatography detectors could be chosen in the analytical method of the present invention, such as a fluorescence detector, an electrochemical detector, a differential detector, an evaporative light-scattering detector, an electrical conductivity detector, a mass spectrometric detector, a charged aerosol detector, or the like.

The analytical method of the present invention includes four steps comprising the preparation of the test solution, the preparation of the control solution, the preparation of the system suitability test solution and the detection.

The preparation of the test solution comprises: taking a proper amount of dexrazoxane or dexrazoxane-containing related preparations, formulating with a diluent into a solution at a concentration of 0.5~2 mg dexrazoxane per 1 mL, used as the test solution;

The preparation of the control solution comprises: taking the test solution, diluting to a volume of 100 times with the diluent, being used as the control solution;

The preparation of the system suitability test solution comprises: taking dexrazoxane or dexrazoxane-containing related preparations, an impurity I control, an impurity II control, an impurity III control at proper amounts, dissolving with the diluent and diluting into a solution containing dexrazoxane 0.5~2 mg, impurities each 5~20 μg per 1 mL, being used as the system suitability test solution;

The detection step comprises: taking the system suitability test solution 10~20 μl, injecting it into the liquid chromatograph, the resolution between the dexrazoxane peak and each adjacent impurity peak should meet the criteria; taking the control solution 10~20 μl, injecting it into the liquid chromatograph, adjusting the detection sensitivity, making the peak height of the chromatographic peak of the main ingredient be 10~20% of the full scale; precisely measuring the test solution 10~20 μl, injecting it into the liquid chromatograph, recording the chromatogram;

wherein the diluent is a hydrochloric acid solution, the chemical structure of each impurity is shown as below:

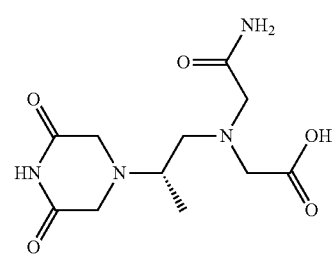

I

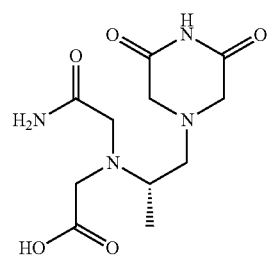

II

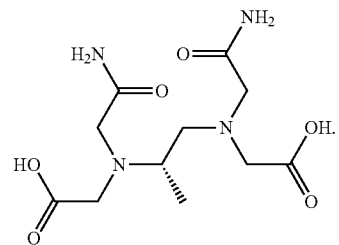

III

Preferably, the analytical method of the present invention includes the following steps:

(1) Preparation of the test solution: taking a proper amount of dexrazoxane or dexrazoxane-containing related preparations, formulating into a solution at a concentration of 0.8~1.1 mg dexrazoxane per 1 mL with a hydrochloric acid solution, being used as the test solution;

(2) Preparation of the control solution: precisely measuring 1 mL test solution prepared in the above (1) and placing it into a 100 mL volumetric flask, diluting to the scale with the hydrochloric acid solution described in (1), being used as the control solution;

(3) Preparation of the system suitability test solution: taking proper amounts of dexrazoxane or dexrazoxane-containing related preparations, impurity I control, impurity II control, impurity III control, dissolving with the hydrochloric acid solution described in (1) and diluting into a solution containing dexrazoxane 0.8~1.1 mg, impurities each 8~12 µg per 1 mL, being used as the system suitability test solution;

(4) detection: taking the system suitability test solution 10 µl, injecting it into the liquid chromatograph, the resolution between the dexrazoxane peak and each adjacent impurity peak should meet the criteria; taking 10 µl of control solution, injecting it into the liquid chromatograph, adjusting the detection sensitivity, making the peak height of the chromatographic peak of the main ingredient be 10~20% of the full scale; precisely measuring 10 µl of test solution, injecting it into the liquid chromatograph, recording the chromatogram.

In a preferable embodiment of the present invention, the analytical method of the present invention includes the following steps:

(1) Preparation of the test solution: taking a proper amount of dexrazoxane or dexrazoxane-containing related preparations, formulating into a solution at a concentration about 1.0 mg dexrazoxane per 1 mL with a hydrochloric acid solution of 0.1 mol/L, being used as the test solution;

(2) Preparation of the control solution: precisely measuring 1 mL test solution prepared in the above (1) and placing it into a 100 mL volumetric flask, diluting to the scale with the hydrochloric acid solution described in (1), being used as the control solution;

(3) Preparation of the system suitability test solution: taking proper amounts of dexrazoxane or dexrazoxane-containing related preparations, impurity I control, impurity II control, impurity III control, dissolving with the hydrochloric acid solution described in (1) and diluting into a solution containing dexrazoxane about 1 mg, impurities each about 10 µg per 1 mL, being used as the system suitability test solution;

(4) Detection: taking the system suitability test solution 10 µl, injecting it into the liquid chromatograph, the resolution between the dexrazoxane peak and each adjacent impurity peak should meet the criteria; taking the control solution 10 µl, injecting it into the liquid chromatograph, adjusting the detection sensitivity, making the peak height of the chromatographic peak of the main ingredient be 10% of the full scale; precisely measuring the test solution 10 µl, injecting it into the liquid chromatograph, recording the chromatogram.

"About" used in the present invention refers to within ±10% of the numerical values.

Compared with the prior art, the analytical method of the present invention allows the main degradation impurities of dexrazoxane to be better retained and separated, the number of theoretical plates of impurities and main peaks to be higher, and more amount of impurities to be detected, but also the validation result of the methodology demonstrated that the method of the present invention is better in terms of repeatability, sensitivity, durability and accuracy, providing an effective and accurate detection method for controlling the qualities of the active pharmaceutical ingredients of dexrazoxane and its preparations.

DETAILED DESCRIPTION

The present invention will be further described below in conjunction with specific embodiments. It should be understood that the following embodiments are only used to further illustrate the present invention, rather than imposing any limits on the scope of the present invention. Dexrazoxane (the active pharmaceutical ingredients), lyophilized preparations of dexrazoxane, impurity I control, impurity II control, impurity III control used in the detailed description of the present invention are all from Jiangsu Aosaikang Pharmaceutical Co., Ltd.; the instrument being used is Agilent 1290 high-performance liquid chromatograph, including G4220B 1290 Bin Pump VL pump, G4212B 1260DAD ultraviolet detector and Thermo Chromeleon 7.2 chromatographic working station. The percentage contents described in the course of elution in the following control examples and embodiments, refer to the volume percent contents.

Control Example 1

1. Chromatographic Conditions

Chromatographic column: Inertsil ODS-SP chromatographic column (150'4.6 mm, 5 µm)

Mobile phase: methanol-0.01 mol/L solution of potassium dihydrogen phosphate (15:85)

Detection wavelength: 208 nm

Flow rate: 1.0 mL/min

Column temperature: 30° C.

2. Experimental Steps

Taking dexrazoxane 10 mg, precisely determined, into which was added 1.0 mL NaOH solution at 0.1 mol/L, left at room temperature for 10 minutes, 0.1 mol/L HCl solution was added to neutralize, and diluting it with a solution of potassium dihydrogen phosphate at 0.01 mol/L to make a solution containing about 1 mg dexrazoxane per 1 mL, which was used as the test solution. [Note: Into the control examples 1-4 was added 1.0 mL NaOH solution at 0.1 mol/L to achieve the effect of alkaline destruction, significantly enhancing the contents of impurity I, impurity II, impurity III in the test solution.

Figure 1:
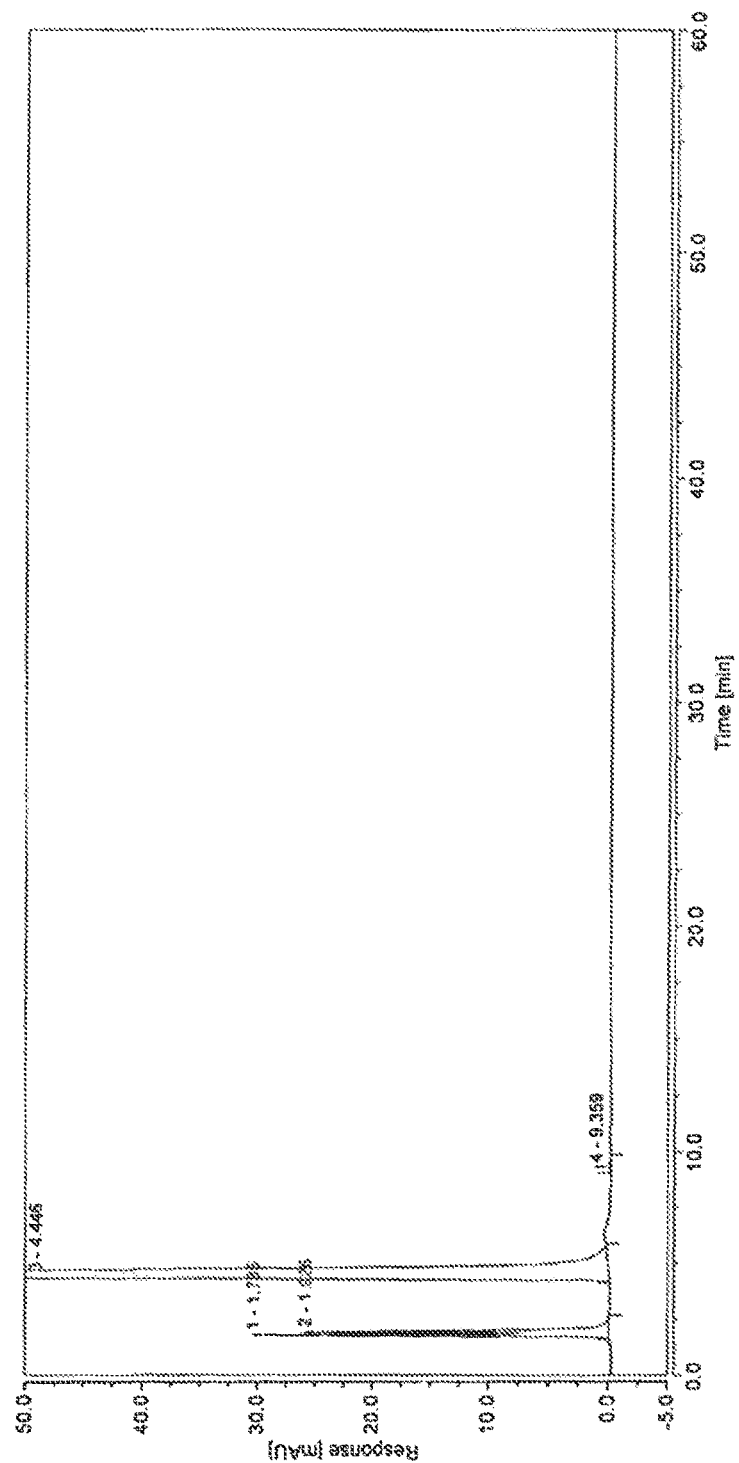
FIG. 1 is the chromatogram under the conditions of the control example 1.

Following the high-performance liquid chromatography (Chinese Pharmacopoeia, Edition 2005, Part 2, Appendix VD), the determination was performed under the above conditions. Taking 10 µl test solution, injecting it into the liquid chromatograph, adjusting the detection sensitivity, making the peak height of the chromatographic peak of the main ingredient to be about 20-30% of the full scale, recording the chromatogram, with the results seen in the accompanying FIG. 1 and Table 1.

As can be seen from the detection results, the chromatographic peaks of impurities III, II, I were overlapped under this condition, the retention time of dexrazoxane was about 4.4 min, and the resolution between impurities was not up to standard. It can be detected by this method that the number of impurities in the sample was not more than 5.

TABLE 1

Results of the test on the separation between dexrazoxane and related substances under the condition of the control example 1

| | Impurity III | | | Impurity II | | | Impurity I | | | Dexrazoxane | | |
|---|---|---|---|---|---|---|---|---|---|---|---|---|
| | Retention Time | Resolution | Number of Theoretical Plates | Retention Time | Resolution | Number of Theoretical Plates | Retention Time | Resolution | Number of Theoretical Plates | Retention Time | Resolution | Number of Theoretical Plates |
| Control Example 1 | Maybe overlapped with impurity II | — | — | 1.786 | 1.00 | 3198 | 1.926 | 13.00 | 2445 | 4.446 | 14.74 | 5826 |

Note:
"—" indicted not detected.

Control Example 2

1. Chromatographic Conditions

Chromatographic column: Dikma Spursil ODS chromatographic column (250*4.6 mm, 5 μm)

Figure 2:
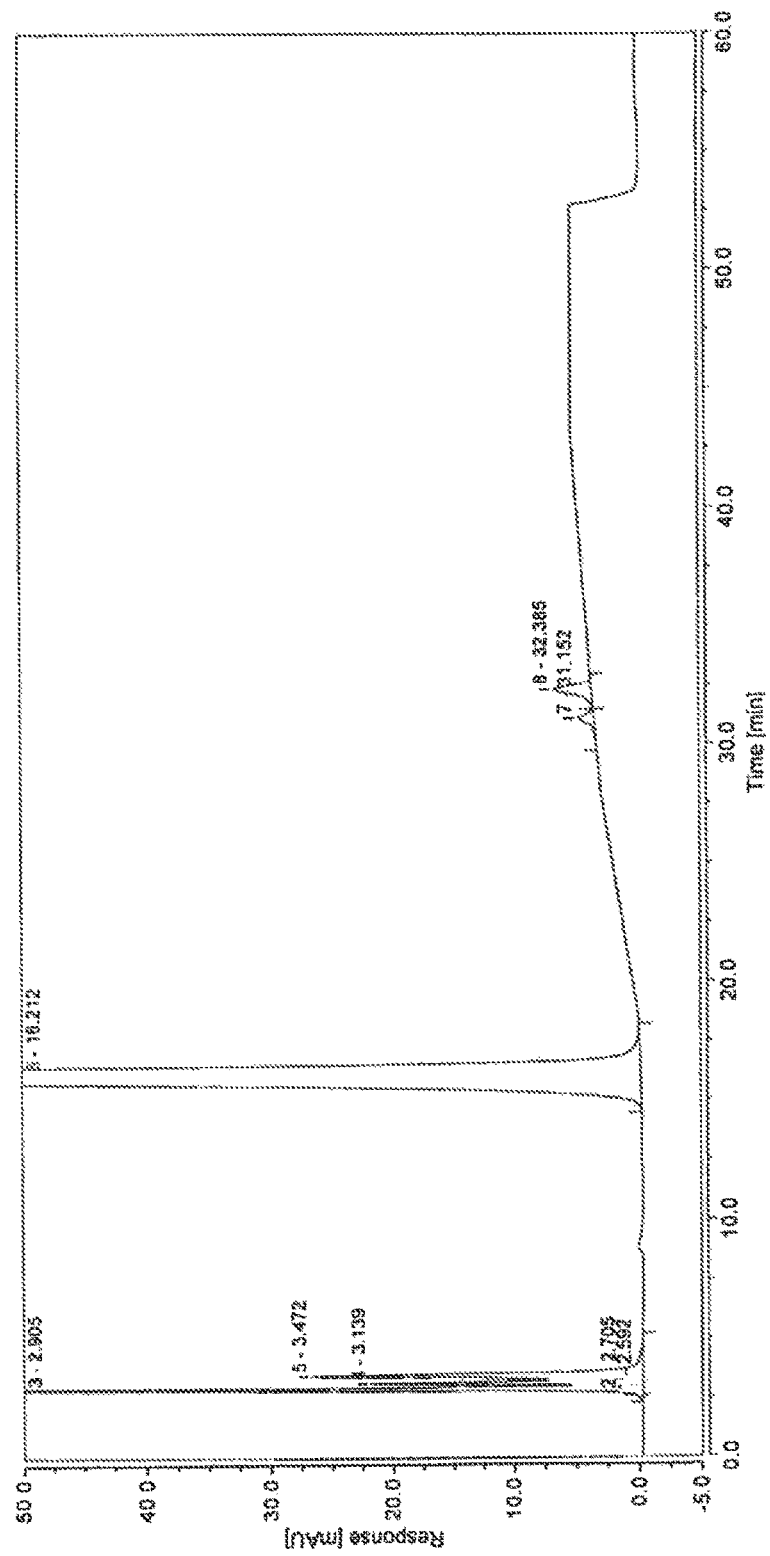
FIG. 2 is the chromatogram under the conditions of the control example 2.

Mobile phase: A is a solution of sodium dihydrogen phosphate at 0.01 mol/L
B is methanol
Detection wavelength: 208 nm
Flow rate: 1.0 mL/min
Column temperature: 30° C.

making the peak height of the chromatographic peak of the main ingredient to be about 20-30% of the full scale, recording the chromatogram, with the results seen in the accompanying FIG. 2 and Table 2.

As can be seen from the detection results, the chromatographic peaks of impurities III, II, I were overlapped under this condition, the chromatographic peak of impurity III was overlapped with the peak of the blank solvent, the retention time of dexrazoxane was about 16.2 min, and the resolution between impurities was not up to standard.

TABLE 2

Results of the test on the separation between dexrazoxane and related substances under the condition of the control example 2

| | Impurity III | | | Impurity II | | | Impurity I | | | Dexrazoxane | | |
|---|---|---|---|---|---|---|---|---|---|---|---|---|
| | Retention Time | Resolution | Number of Theoretical Plates | Retention Time | Resolution | Number of Theoretical Plates | Retention Time | Resolution | Number of Theoretical Plates | Retention time | Resolution | Number of Theoretical Plates |
| Control Example 2 | 2.905 (overlapped with the peak of the blank solvent) | 1.28 | 6764 | 3.139 | 1.22 | 3168 | 3.472 | 24.41 | 1804 | 16.212 | 22.90 | 8117 |

Gradient elution conditions:

| Time (minutes) | Mobile phase A (%) | Mobile phase B (%) |
|---|---|---|
| 0 | 96 | 4 |
| 15 | 96 | 4 |
| 25 | 90 | 10 |
| 40 | 85 | 15 |
| 50 | 85 | 15 |
| 50.01 | 96 | 4 |
| 60 | 96 | 4 |

2. Experimental Steps

Taking dexrazoxane 10 mg, precisely determined, into which was added 1.0 mL NaOH solution at 0.1 mol/L, left at room temperature for 10 minutes, 0.1 mol/L HCl solution was added to neutralize, and diluting it with a solution of potassium dihydrogen phosphate at 0.01 mol/L to make a solution containing about 1 mg dexrazoxane per 1 mL, which was used as the test solution.

Following the high-performance liquid chromatography (Chinese Pharmacopoeia, Edition 2015, Part 4, Appendix 0512), the determination was performed under the above conditions. Taking 10 μl test solution, injecting it into the liquid chromatograph, adjusting the detection sensitivity, Control Example 3

1. Chromatographic Conditions

Chromatographic column: Waters XBridge Hilic chromatographic column (250*4.6 mm, 5 μm)

Mobile phase: A is a solution of ammonium acetate at 0.01 mol/L
B is acetonitrile
Detection wavelength: 208 nm
Flow rate: 1.0 mL/min
Column temperature: 30° C.
Gradient elution conditions:

| Time (minutes) | Mobile phase A (%) | Mobile phase B (%) |
|---|---|---|
| 0 | 5 | 95 |
| 30 | 50 | 50 |
| 50 | 50 | 50 |
| 50.01 | 5 | 95 |
| 60 | 5 | 95 |

2. Experimental Steps

Taking dexrazoxane 10 mg, precisely determined, into which was added 1.0 mL NaOH solution at 0.1 mol/L, left at room temperature for 10 minutes, 0.1 mol/L HCl solution was added to neutralize, and diluting it with a solution of ammonium acetate at 0.01 mol/L to make a solution containing about 1 mg dexrazoxane per 1 mL, which was used as the test solution.

Figure 3:
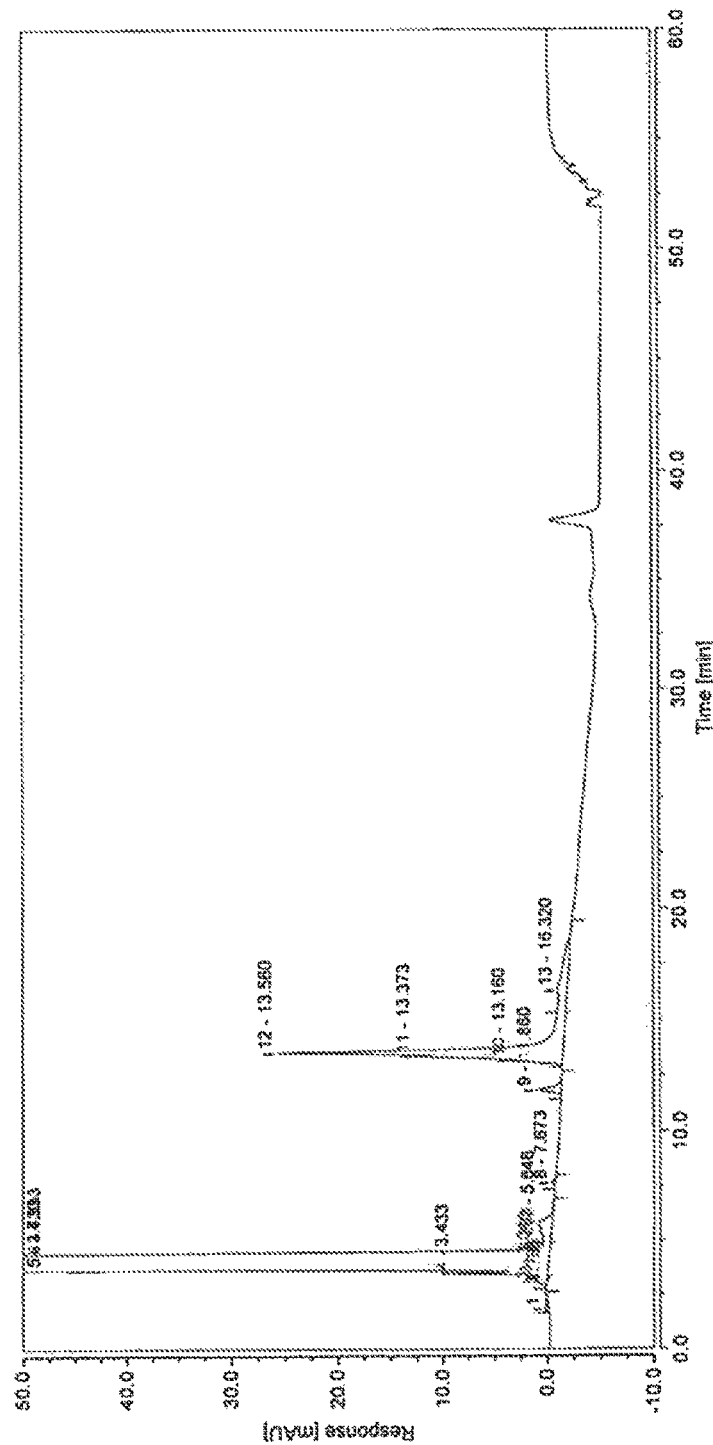
FIG. 3 is the chromatogram under the conditions of the control example 3.

Following the high-performance liquid chromatography (Chinese Pharmacopoeia, Edition 2015, Part 4, Appendix 0512), the determination was performed under the above conditions. Taking 10 μl test solution, injecting it into the liquid chromatograph, adjusting the detection sensitivity, making the peak height of the chromatographic peak of the main ingredient to be about 20-30% of the full scale, recording the chromatogram, with the results seen in the accompanying FIG. 3.

It was shown from the detection results that the retention time of the main peak was very short and the main peak was splitted, the peak shape of the impurities was not desirable solution containing about 1 mg dexrazoxane per 1 mL, which was used as the test solution.

Figure 4:
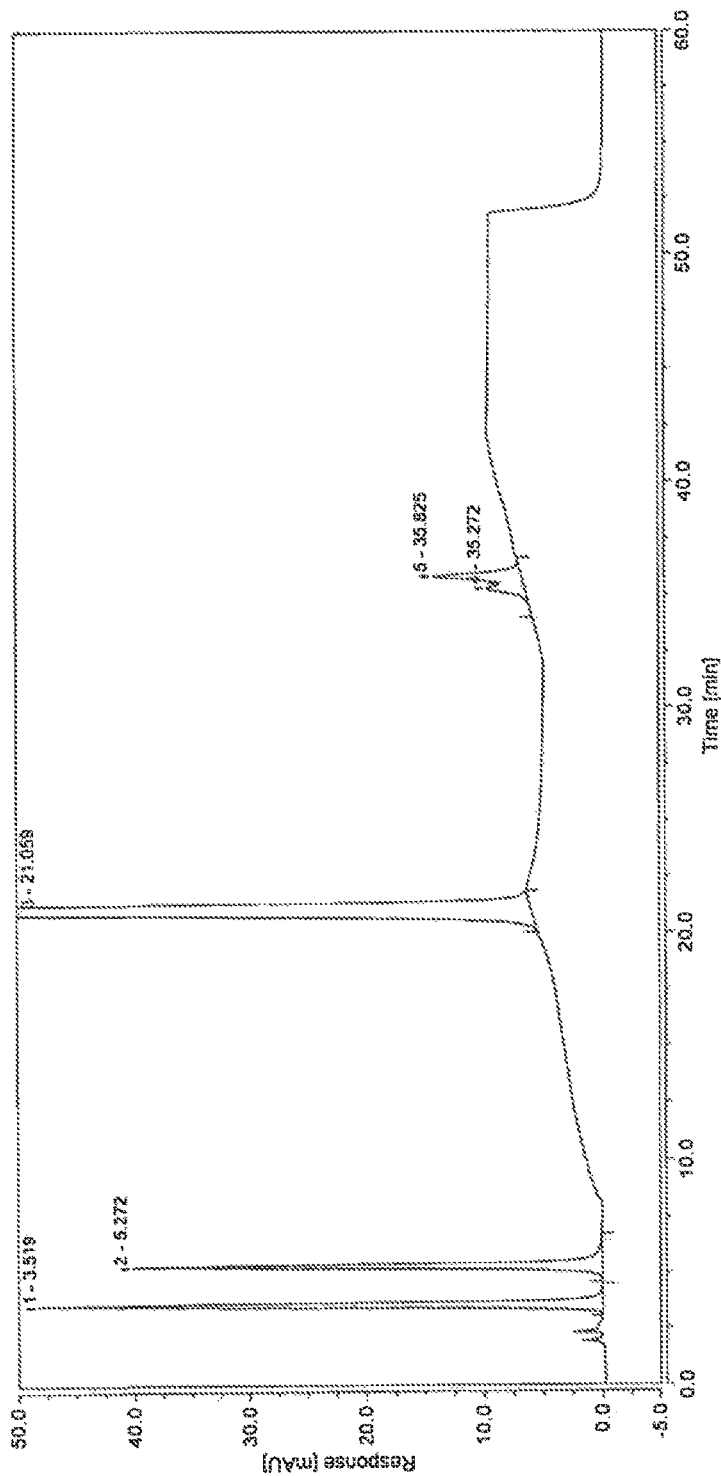
FIG. 4 is the chromatogram under the conditions of the control example 4.

Following the high-performance liquid chromatography (Chinese Pharmacopoeia, Edition 2015, Part 4, Appendix 0512), the determination was performed under the above conditions. Taking 10 μl test solution, injecting it into the liquid chromatograph, adjusting the detection sensitivity, making the peak height of the chromatographic peak of the main ingredient to be about 20-30% of the full scale, recording the chromatogram, with the results seen in the accompanying FIG. 4 and Table 3.

According to detection results, the chromatographic peak of impurity III was overlapped with the peak of the blank solvent, and this method can't meet the criteria in Chinese Pharmacopoeia.

TABLE 3

Results of the test on the separation between dexrazoxane and related substances under the condition of the control example 4

| | Impurity III | | | Impurity II | | | Impurity I | | | Dexrazoxane | | |
|---|---|---|---|---|---|---|---|---|---|---|---|---|
| | Retention Time | Resolution | Number of Theoretical Plates | Retention Time | Resolution | Number of Theoretical Plates | Retention Time | Resolution | Number of Theoretical Plates | Retention Time | Resolution | Number of Theoretical Plates |
| Control Example 4 | — (overlapped with the peak of the blank solvent) | — | — | 3.519 | 5.47 | 1775 | 5.272 | 47.26 | 4681 | 21.059 | — | — |

Note:
"—" indicted not detected or no data obtained.

and the baseline was not smooth. This method can't meet the criteria in Chinese Pharmacopoeia.

Control Example 4

1. Chromatographic Conditions

Chromatographic column: YMC-Pack ODS-AQ chromatographic column (150*4.6 mm, 5 μm)

Mobile phase: A is a solution of potassium dihydrogen phosphate at 0.01 mol/L

B is methanol

Detection wavelength: 208 nm

Flow rate: 1.0 mL/min

Column temperature: 20° C.

Gradient elution conditions:

| Time (minutes) | Mobile phase A (%) | Mobile phase B (%) |
|---|---|---|
| 0 | 100 | 0 |
| 5 | 100 | 0 |
| 10 | 96 | 4 |
| 20 | 90 | 10 |
| 30 | 90 | 10 |
| 40 | 80 | 20 |
| 50 | 80 | 20 |
| 50.01 | 100 | 0 |
| 60 | 100 | 0 |

2. Experimental Steps

Taking dexrazoxane 10 mg, precisely determined, into which was added 1.0 mL NaOH solution at 0.1 mol/L, left at room temperature for 10 minutes, 0.1 mol/L HCl solution was added to neutralize, and diluting it with a solution of potassium dihydrogen phosphate at 0.01 mol/L to make a Embodiment 1

1. Chromatographic Conditions

Chromatographic column: Waters Atlantis T3 chromatographic column (250*4.6 mm, 5 μm)

Mobile phase: A is a solution of $KH_2PO_4$ at 10 mmol/L (pH4.5~5)

B is methanol

Detection wavelength: 208 nm

Flow rate: 1.0 mL/min

Column temperature: 15° C.

Gradient elution conditions:

| | Time (minutes) | Mobile phase A (%) | Mobile phase B (%) |
|---|---|---|---|
| First stage | 0 | 100 | 0 |
| | 15 | 100 | 0 |
| | 45 | 70 | 30 |
| | 50 | 70 | 30 |
| | 50.01 | 100 | 0 |
| | 60 | 100 | 0 |

2. Experimental Steps

Taking the lyophilized preparations of dexrazoxane, precisely determined, into which was added a hydrochloric acid solution at 0.1 mol/L, and quantitatively diluted to a solution containing about 1 mg dexrazoxane per 1 mL, which was used as the test solution. 1 mL test solution was precisely measured and placed into a 100 mL volumetric flask, diluted to the scale with 0.1 mol/L hydrochloric acid, shaked well, and used as the control solution. Additionally, taking proper amounts of the lyophilized preparations of dexrazoxane, impurity I, impurity II, impurity III controls, into which was added a hydrochloric acid solution at 0.1 mol/L, and diluted to a solution containing about 1 mg dexrazoxane and impurities each 10 μg per 1 mL, which was used as the system suitability test solution.

Figure 5:
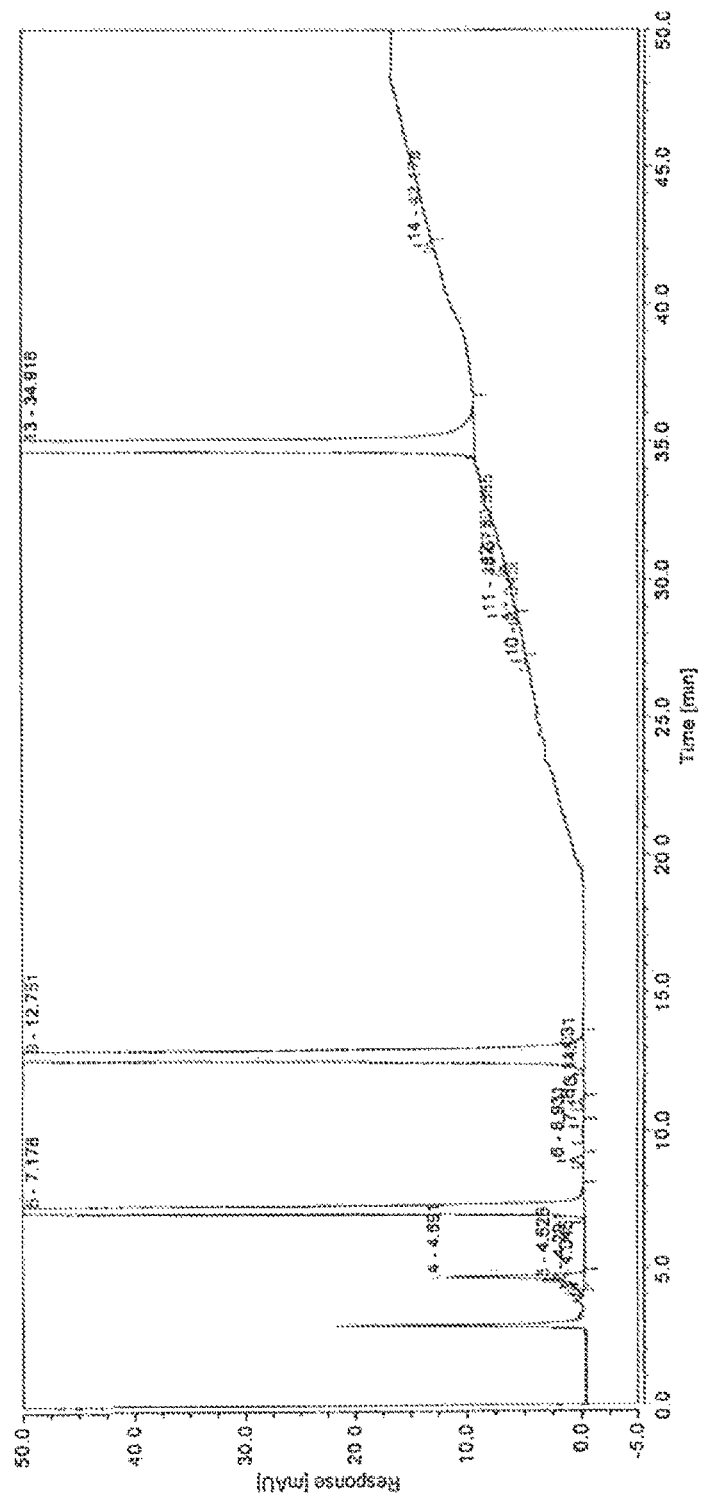
FIG. 5 is the chromatogram of the system suitability test under the conditions of the Embodiment 1.

Following the high-performance liquid chromatography (Chinese Pharmacopoeia, Edition 2015, Part 4, Appendix 0512), the determination was performed under the above conditions. Taking 10 μl of the system suitability test solution, injecting it into the liquid chromatograph, recording the chromatogram, with the results seen in the accompanying FIG. 5 and Table 4.

As can be seen from the detection results, impurity III, impurity II, impurity I and dexrazoxane are separated out successively, the retention time was 4.7 min, 7.2 min, 12.7 min, 34.9 min, respectively, and the resolution between impurities as well as between impurities and main peaks were all greater than 5, meeting the criteria in Chinese Pharmacopoeia. Compared with the control examples, the numbers of theoretical plates of impurities and main peaks in the method of the present invention were higher, and more impurities could be detected in the sample, with a general number of 15~25.

TABLE 4

Results of the system suitability test on the separation between dexrazoxane and related substances under the condition of Embodiment 1

| | Impurity III | | | Impurity II | | | Impurity I | | | Dexrazoxane | | |
|---|---|---|---|---|---|---|---|---|---|---|---|---|
| | Retention Time | Resolution | Number of Theoretical Plates | Retention Time | Resolution | Number of Theoretical Plates | Retention Time | Resoluton | Number of Theoretical Plates | Retention Time | Resolution | Number of Theoretical Plates |
| Embodiment 1 | 4.691 | 11.70 | 9960 | 7.178 | 6.84 | 14529 | 12.751 | 44.04 | 16487 | 34.918 | 26.32 | 253171 |

Figure 6:
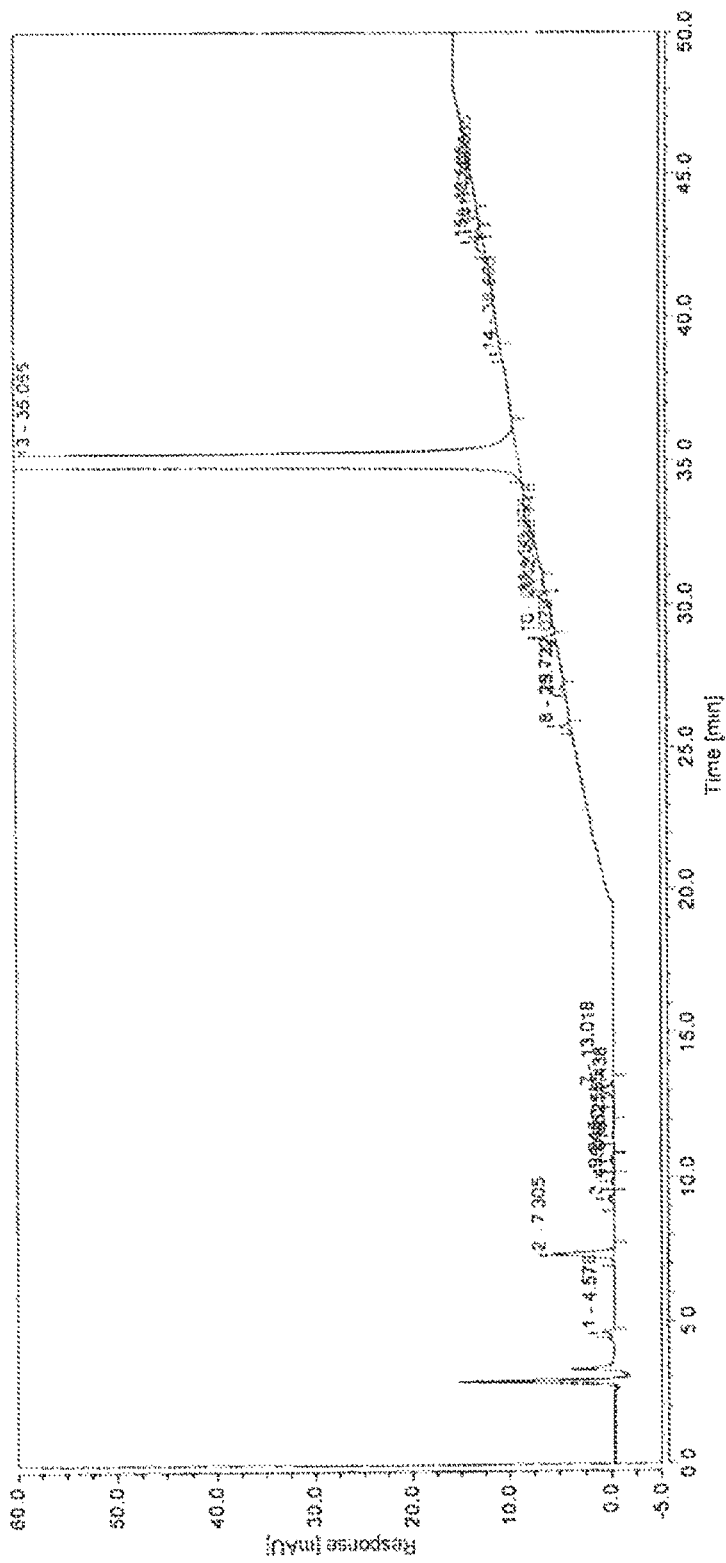
FIG. 6 is the chromatogram of the test solution under the conditions of the Embodiment 1.

Taking the control solution 10 μl, injecting it into the liquid chromatograph, adjusting the detection sensitivity, making the peak height of the chromatographic peak of the main ingredient to be about 10% of the full scale. Precisely measuring the test solution and the control solution 10 μl each, respectively being injected into the liquid chromatograph, and recording the chromatogram, wherein the chromatogram of the test solution was shown in the accompanying FIG. 6. Detection results show that the impurity I was not detected, the resolutions between impurity II and I as well as between the impurities and the main peaks were both well, thus meeting the criteria in Chinese Pharmacopoeia.

Embodiments 2~9

1. Chromatographic Conditions

The conditions of the chromatographic column and the gradient elution employed in the chromatographic conditions in Embodiments 2~9 were the same as those in Embodiment 1, and other chromatographic conditions were shown as below:

| | Mobile Phase | Detection Wavelength | Flow Rate | Column Temperature |
|---|---|---|---|---|
| Embodiment 2 | A: $KH_2PO_4$ solution (8 mmol/L, pH4.5~5)<br>B: Methanol | 208 nm | 1.0 mL/min | 15 |
| Embodiment 3 | A: $KH_2PO_4$ solution (12 mmol/L, pH 4.5~5)<br>B: Methanol | 208 nm | 1.0 mL/min | 15 |
| Embodiment 4 | A: $KH_2PO_4$ solution (10 mmol/L, pH 4.5~5)<br>B: Methanol | 203 nm | 1.0 mL/min | 15 |
| Embodiment 5 | A: $KH_2PO_4$ solution (10 mmol/L, pH 4.5~5)<br>B: Methanol | 213 nm | 1.0 mL/min | 15 |
| Embodiment 6 | A: $KH_2PO_4$ solution (10 mmol/L, pH 4.5~5)<br>B: Methanol | 208 nm | 0.8 mL/min | 15 |
| Embodiment 7 | A: $KH_2PO_4$ solution (10 mmol/L, pH 4.5~5)<br>B: Methanol | 208 nm | 1.2 mL/min | 15 |
| Embodiment 8 | A: $KH_2PO_4$ solution (10 mmol/L, pH 4.5~5)<br>B: Methanol | 208 nm | 1.0 mL/min | 10 |
| Embodiment 9 | A: $KH_2PO_4$ solution (10 mmol/L, pH 4.5~5)<br>B: Methanol | 208 nm | 1.0 mL/min | 20 |

2. Experimental Steps

Taking the lyophilized preparations of dexrazoxane, the liquid chromatography was performed according to the experimental steps described in Embodiment 1 under the chromatographic conditions of the above embodiments 2~9. The results of the test solution detection were shown in Table 5:

TABLE 5

Results of the system suitability test on the separation between dexrazoxane and related substances under the conditions of Embodiment 2~9

| | Impurity III | | | Impurity II | | | Impurity I | | | Dexrazoxane | | |
| --- | --- | --- | --- | --- | --- | --- | --- | --- | --- | --- | --- | --- |
| | Retention Time | Resolution | Number of Theoretical Plates | Retention Time | Resolution | Number of Theoretical Plates | Retention Time | Resolution | Number of Theoretical Plates | Retention Time | Resolution | Number of Theoretical Plates |
| Embodiment 2 | — | — | — | 7.190 | 3.91 | 9091 | 12.817 | 2.10 | 9887 | 34.904 | — | 142908 |
| Embodiment 3 | — | — | — | 7.182 | 5.14 | 8431 | 12.782 | 17.43 | 9166 | 34.902 | 14.94 | 133939 |
| Embodiment 4 | — | — | — | 7.183 | 4.98 | 9708 | 12.783 | 32.84 | 10589 | 34.910 | — | 112941 |
| Embodiment 5 | — | — | — | 7.177 | 5.03 | 9658 | 12.777 | 8.86 | 10583 | 34.904 | — | 183775 |
| Embodiment 6 | — | — | — | 8.946 | 5.57 | 11717 | 15.920 | 18.06 | 12748 | 37.053 | 20.08 | 143025 |
| Embodiment 7 | — | — | — | 5.989 | 4.78 | 8936 | 10.663 | — | 9799 | 33.316 | 16.21 | 155680 |
| Embodiment 8 | — | — | — | 7.725 | 5.78 | 9932 | 14.225 | 27.09 | 10917 | 35.625 | 17.24 | 153198 |
| Embodiment 9 | — | — | — | 6.717 | 4.67 | 10987 | 11.584 | — | 12092 | 34.218 | 21.73 | 157645 |

Note:
"—" indicted not detected or no data obtained.

It was shown from the results that the resolutions between the main peak and the impurity peak and the number of theoretical plates both met the criteria when there were slight changes in the concentration of the buffer, the wavelength, the flow rate and the column temperature, and the durability for the method of the present invention would be good.

In addition, the method of the present invention was validated in the terms of methodology through various tests on the specificity, the quantitation limit and the detection limit, the repeatability, the accuracy, or the like, and the results indicated that the method of the present invention had a good specificity, a high sensitivity, and were well in both the repeatability and the accuracy, capable of meeting the need of the analytical detection on the active pharmaceutical ingredients of dexrazoxane and their preparations.

The invention claimed is:

1. A high performance liquid chromatography method used for dexrazoxane-related substances, comprising:
   performing a gradient elution via a low-density bonding reversed-phase chromatographic column resistant to pure water, where the gradient elution is carried out with a mobile phase A and a mobile phase B as eluents; wherein
   the mobile phase A is a buffer;
   the mobile phase B is an organic solvent; and
   the gradient elution comprises at least a first stage that is 15-30 minutes in duration in which the volume of the mobile phase A that is introduced into the low-density bonding reversed-phase C18 chromatographic column is not lower than is such that the mobile phase A represents 90% or more of the total volume of all eluents of the mobile phase being introduced into the low-density bonding reversed-phase C18 chromatographic column.

2. The method of claim 1, wherein the low-density bonding reversed-phase C18 chromatographic column resistant to pure water is Waters Atlantis T3 or Waters ACQUITY HSS T3.

3. The method of claim 2, wherein the low-density bonding reversed-phase C18 chromatographic column resistant to pure water is Waters Atlantis T3.

4. The method of claim 1, wherein
   the buffer is selected from a buffered salt solution of 1-50 mmol/L at a pH of 1-6, of potassium dihydrogen phosphate, sodium dihydrogen phosphate, disodium hydrogen phosphate, dipotassium hydrogen phosphate, diammonium hydrogen phosphate or ammonium dihydrogen phosphate; and
   the organic solvent is selected from methanol, acetonitrile or isopropanol.

5. The method of claim 4, wherein the buffer is a potassium dihydrogen phosphate solution of 5-15 mmol/L at a pH of 3.5-5.5, the organic solvent is methanol or acetonitrile.

6. The method of claim 4, wherein the buffer is a potassium dihydrogen phosphate solution of 8-12 mmol/L at a pH of 4.5-5, the organic solvent is methanol.

7. The method of claim 1, wherein
   the mobile phase A represents 95% or more of the total volume of all the eluents of the mobile phase introduced into the low-density bonding reversed-phase C18 chromatographic column in the first stage of the gradient elution, and the duration of the first stage of the gradient elution ranges from 15-20 minutes.

8. The method of claim 1, wherein
   the gradient elution further comprises a second, a third and a fourth stage;
   the only eluent introduced into the low-density bonding reversed-phase C18 chromatographic column during the first stage of the gradient elution is the mobile phase A, the first stage ending 15 minutes after it begins;
   during the second stage, which lasts for a duration of 30 minutes and immediately follows the first stage, the volume percent of the mobile phase A introduced into the low-density bonding reversed-phase C18 chromatographic column is adjusted from 100% to a predetermined volume percent of n %, where 10≤n≤90, and, at the same time, the volume percent of the mobile phase B introduced into the low-density bonding reversed-phase C18 chromatographic column in the second stage of the gradient elution is adjusted from 0% to a volume percent of (100−n) %, wherein
   during the entire second stage the volume percentages of the mobile phase A and the mobile phase B are adjusted in a linear manner such that the predetermined volume percent of n % for the mobile phase A is achieved at the 30 minute mark of the second stage;

during the third stage, which lasts for a duration of 5 minutes and immediately follows the second stage, the volume percent of the mobile phase A introduced into the low-density bonding reversed-phase C18 chromatographic column is maintained at the predetermined volume percent of n % that was achieved at the end of the second stage, and the volume percent of the mobile phase B introduced into the low-density bonding reversed-phase C18 chromatographic column is maintained at the volume percent of (100−n) % that was achieved at the end of the second stage; and during the fourth stage, which lasts for a duration of 10 minutes and immediately follows the third stage, in the initial 0.01 minute of the fourth stage the volume percent of the mobile phase A introduced into the low-density bonding reversed-phase C18 chromatographic column is increased from the predetermined volume percent of n % that was maintained for 5 minutes in the third stage to 100%, and at the same time, the volume percent of the mobile phase B introduced into the low-density bonding reversed-phase C18 chromatographic column is reduced to 0%, and then for the remaining 9.99 minutes of the fourth stage the only eluent introduced into the low-density bonding reversed-phase C18 chromatographic column is the mobile phase A.

9. The method of claim 8, wherein 50≤n≤80.
10. The method of claim 8, wherein 60≤n≤80.
11. The method of claim 1, wherein
the flow rate of the mobile phase is 0.6-1.5 mL/min, and/or
the temperature of the chromatographic column is 5-20° C., and/or
the ultraviolet detector is employed as the detector, with a detection wavelength of 200-220 nm.
12. The method of claim 11, wherein the flow rate of the mobile phase is 0.8-1.2 mL/min; the temperature of the chromatographic column is 10-20° C.; the detection wavelength is 203-213 nm.
13. The method of claim 1, further comprising:
preparing a test solution from an amount of dexrazoxane or dexrazoxane-containing related preparations and a diluent, the test solution having a concentration of 0.5-2 mg dexrazoxane per 1 mL;
preparing a control solution from the test solution by diluting an aliquot of the test solution to a volume of 100 times that of the aliquot with a hydrochloric acid solution;
preparing a system suitability test solution from a hydrochloric acid solution and an amount of dexrazoxane or dexrazoxane-containing related preparations, an impurity I control, an impurity II control, and an impurity III control the system suitability test solution containing dexrazoxane at 0.5-2 mg, impurity I at 5-20 µg, impurity II at 5-20 µg, and impurity III at 5-20 µg per 1 mL;

injecting 10-20 µl of the system suitability test solution into a liquid chromatograph that comprises the low-density bonding reversed-phase C18 chromatographic column, injecting 10-20 µl of the control solution into the liquid chromatograph, and injecting 10-20 µl of test solution into the liquid chromatograph and recording the chromatogram;

wherein the diluent is a hydrochloric acid solution, the chemical structures of impurity I, impurity II, impurity III are shown as below:

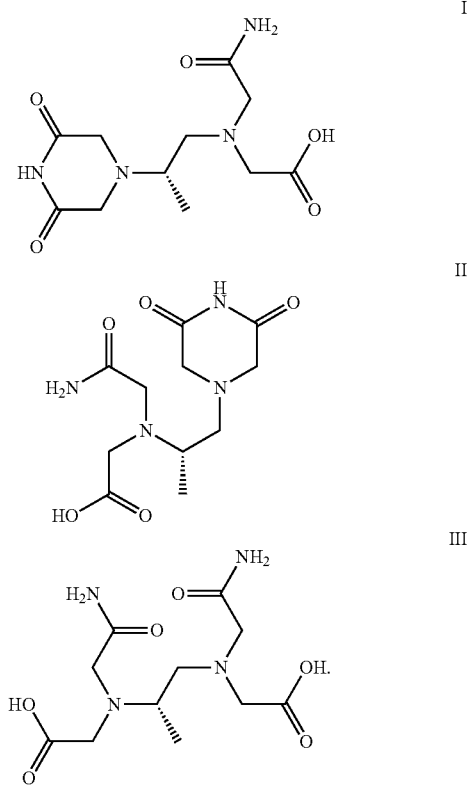

14. The method of claim 13, wherein
the test solution has a concentration of 0.8-1.1 mg of the dexrazoxane per 1 mL;
the control solution contains the dexrazoxane at 0.8-1.1 mg, the impurity I at 8-12 µg, the impurity II at 8-12 µg, and the impurity III at 8-12 µg per 1 mL;
10 µl of the system suitability test solution 10 µl is injected, into the liquid chromatograph; 10 µl of the control solution 10 µl is injected into the liquid chromatograph; and 10 µl of the test solution is injected into the liquid chromatograph.
15. The method of claim 1, further comprising detecting the presence of dexrazoxane and/or one or more impurities in a sample or dexrazoxane-containing preparations.

* * * * *